United States Patent [19]
Mir et al.

[11] Patent Number: 5,674,267
[45] Date of Patent: Oct. 7, 1997

[54] ELECTRIC PULSE APPLICATOR USING PAIRS OF NEEDLE ELECTRODES FOR THE TREATMENT OF BIOLOGICAL TISSUE

[75] Inventors: Lluis Mir, Verrieres-le-Buisson; Stephane Orlowski, Bourg-la-Reine; Michel Siros, Antony, all of France

[73] Assignee: Centre National de la Recherche Scientifique, Paris, France

[21] Appl. No.: 525,656

[22] PCT Filed: Mar. 24, 1994

[86] PCT No.: PCT/FR94/00330

§ 371 Date: Dec. 4, 1995

§ 102(e) Date: Dec. 4, 1995

[87] PCT Pub. No.: WO94/22526

PCT Pub. Date: Oct. 13, 1994

[30] Foreign Application Priority Data

Mar. 30, 1993 [FR] France ................... 93 03688

[51] Int. Cl.$^6$ .................. A61N 1/18; A61N 1/20; A61N 1/30
[52] U.S. Cl. .................. 607/72; 604/21; 607/3
[58] Field of Search .............. 607/2, 3, 72; 604/20, 604/21

[56] References Cited

U.S. PATENT DOCUMENTS

| | | | |
|---|---|---|---|
| 1,653,819 | 12/1927 | Northcott et al. | |
| 4,262,672 | 4/1981 | Kief | 607/72 |
| 4,907,601 | 3/1990 | Frick | 607/72 |
| 5,058,605 | 10/1991 | Slovak | 607/72 |
| 5,273,525 | 12/1993 | Hofmann | 604/21 |
| 5,328,451 | 7/1994 | Davis et al. | 604/20 |
| 5,425,752 | 6/1995 | Vu'Nguyen | 607/72 |
| 5,439,440 | 8/1995 | Hofmann | 604/20 |

FOREIGN PATENT DOCUMENTS

| | | | |
|---|---|---|---|
| 0378132 | 7/1990 | European Pat. Off. | A61N 1/30 |
| 863111 | 1/1953 | Germany. | |
| 4000893A | 7/1991 | Germany | 607/72 |

OTHER PUBLICATIONS

Compte Rendu Academie Des Sciences, vol 313, No. 111, Nov. 27, 1991, Paris, France, article entitled "L'électrochimiothérapie, un nouveau traitemente antitumoral: premier essai clinique"(Electrochemotherapy, a new antitumor treatment: first clinical trial).

*Primary Examiner*—William E. Kamm
*Assistant Examiner*—Carl H. Layno
*Attorney, Agent, or Firm*—Greenblum & Bernstein P.L.C.

[57] ABSTRACT

An electric pulse applicator for the treatment of biological tissue applies an electric field to the cells of biological tissue to modify the properties of their membranes. The electric pulse applicator includes electrodes and a pulse generator. The electrodes comprise at least three needles which are introduced into the tissue to be treated and which define a treatment volume. The needles are formed into pairs and a selector switch directs successive pulses produced by the pulse generator to each different pair of needles.

21 Claims, 5 Drawing Sheets

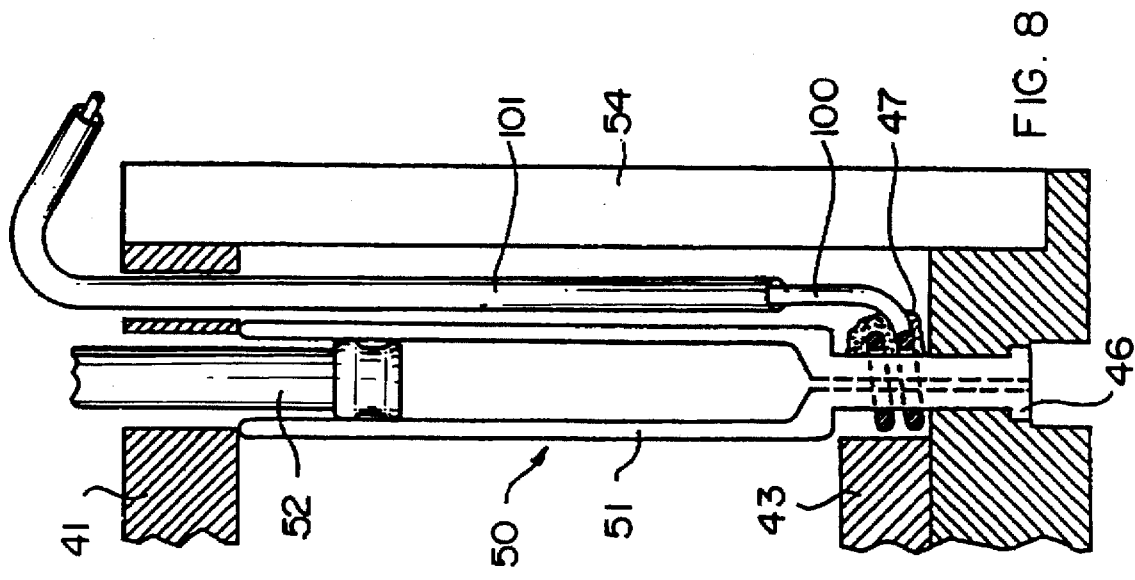
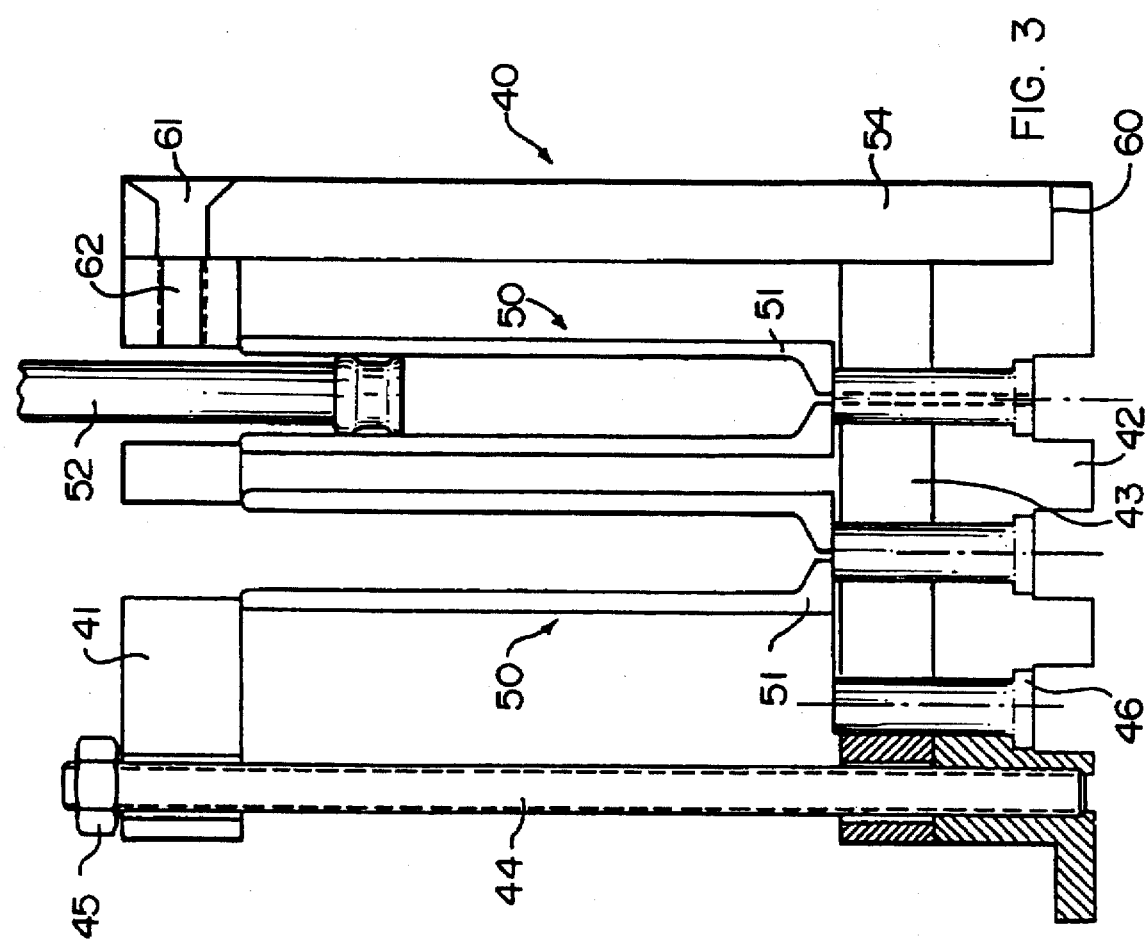

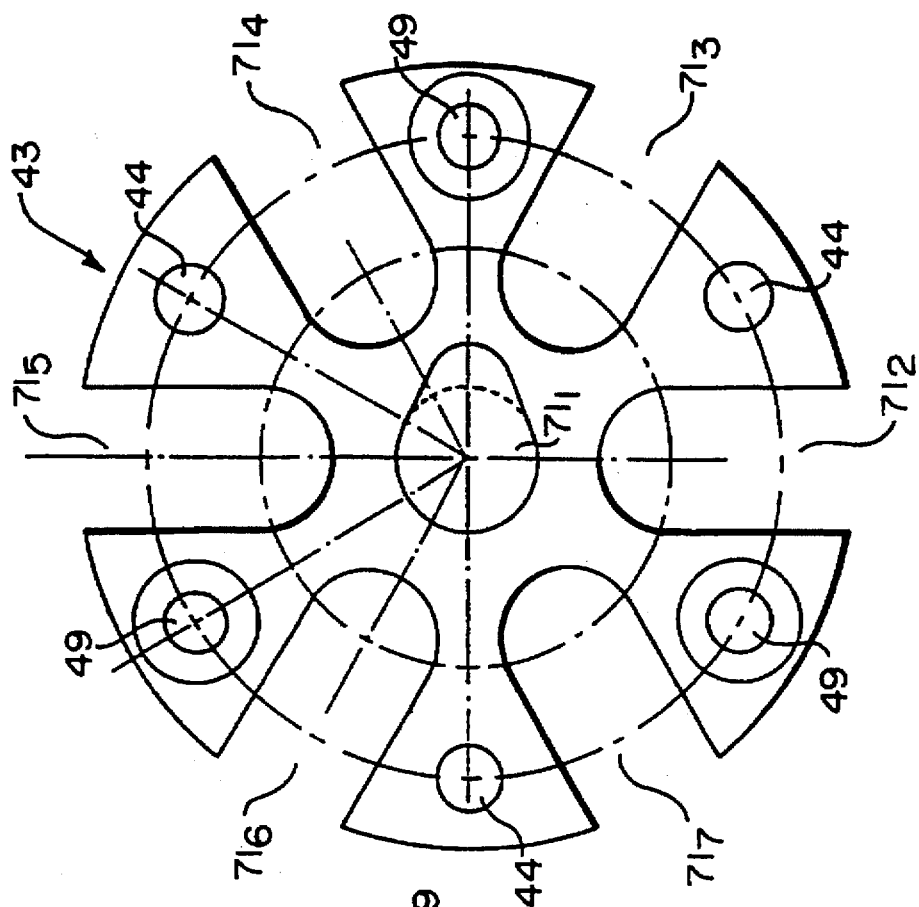
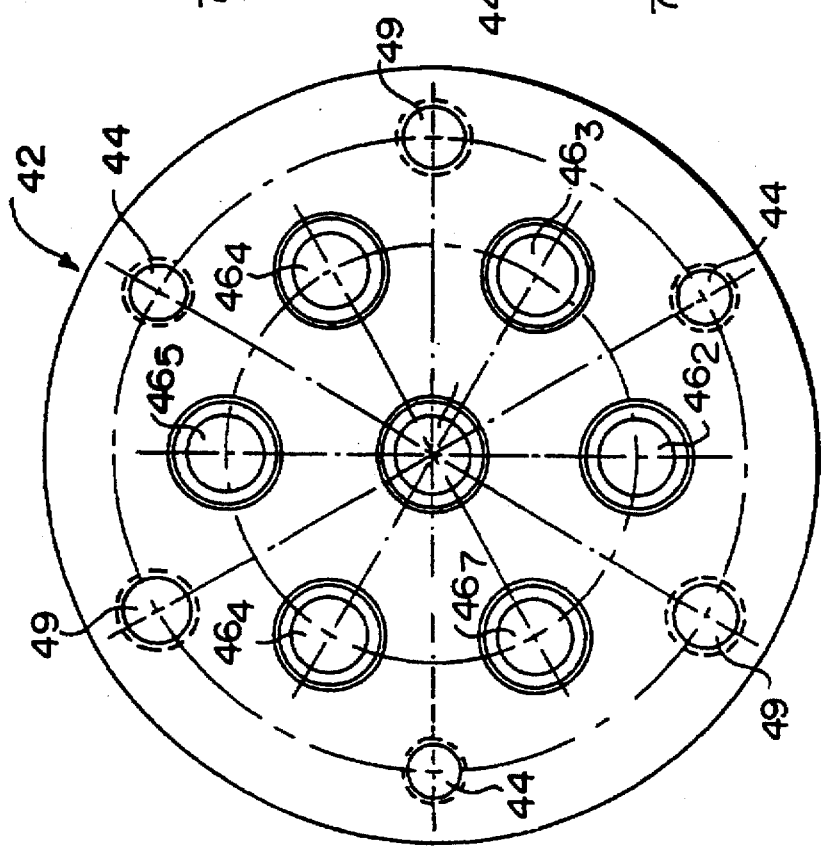
FIG. 7
FIG. 6

ELECTRIC PULSE APPLICATOR USING PAIRS OF NEEDLE ELECTRODES FOR THE TREATMENT OF BIOLOGICAL TISSUE

BACKGROUND OF THE INVENTION

1. Field of the Invention

This invention relates to a device for applying electric pulses for the treatment of biological tissue. It is particularly intended for the implementation of electrochemotherapy.

2. Discussion of Background

Electrochemotherapy is a new therapeutic method that has been developed in particular for the treatment of cancers.

Indeed, it has been found that a certain number of active substances have difficulty in traversing the membrane of the cells that the are intended for.

To overcome this difficulty, it is often necessary to increase the doses of the substances provided, this often being difficult and nearly always having unwanted side effects.

It has recently been shown that the permeability of a cell's plasma membrane can be increased by applying electric pulses to the cell.

Electrochemotherapy takes advantage of this possibility by combining the injection of an active substance with the application of short, intense electric pulses. The penetration of the active substance into the cells subjected to the electric field is thus facilitated. Electrochemotherapy has, for example, been used to treat tumors using bleomycin. The antitumor effects of bleomycin combined with the electric pulses can be potentiated by injections of immunostimulants such as interleukines, for example interleukine-2, or injections of medicamentous compositions such as syngenic, allogenic or xenogenic cells that secrete interleukines, for example interleukine-2. The injection of these substances or compositions is especially effective if it is done locally at the level of the tumor, treated beforehand by electrochemotherapy.

The electric fields required to implement electrochemotherapy have, to date, been obtained by applying pulses between two external electrodes placed, as far as possible, on either side of the tumor to be treated.

The electrical contact of these electrodes with the skin is ensured by a conductive gel.

Such a technique is described, for example, in the "Compte-Rendu de l'Académie des Sciences de Paris" t.313, series III, pages 613-618, 1991: "L'électrochimiothérapie, un nouveau traitement antitumor: premier essai clinique" (Electrochemotherapy, a new antitumor treatment: first clinical trial) Lluis M. MIR et al.

The electrodes used to date for applying electric pulses cannot uniformly distribute the electric fields produced throughout the whole volume to be treated, and require, for the chemotherapeutic part, that the antitumor medicamentous product be injected into the patient's whole body.

SUMMARY OF THE INVENTION

The object of this invention is an applicator which improves the distribution and control of electric fields produced for electrochemotherapy.

Another object of the invention is to propose an electric pulse applicator whose use avoids or limits the side effects produced.

A further object of the invention is to propose an electric pulse applicator for electrochemotherapy that may be used several times without causing unwanted lesions of healthy tissue close to the tumor, for example of the skin.

A further object of the invention is to propose a compact, sterilizable, autoclavable device capable of withstanding high voltage.

With this object in view, the invention therefore relates to an electric pulse applicator for the treatment of biological tissue allowing an electric field to be applied to cells of biological tissue so as to modify the properties of their membrane. This applicator comprises electrodes and a pulse generator.

According to the invention, the electrodes comprise at least three needles which are intended to be introduced into the tissue to be treated and to define a treatment volume, said needles forming in twos pairs of needles, and a needle selector switch which sends the pulses produced by the pulse generator successively onto the different pairs of needles.

According to different preferred embodiments, the electric pulse applicator for the treatment of biological tissue of the invention comprises the following characteristics, taken alone or in any technically feasible combination:

- the needles of the electrodes are fixed onto a needle applicator in an interchangeable way;
- the needles each comprise a base and a stem terminated by a point, the base ensuring the fixing of the needle onto the needle holder, the point ensuring the penetration of the needle into the tissue, one or more portions of the stem being surrounded by an insulating sleeve;
- one portion of the insulating sleeve of the needles is intended to remain implanted in the tissue;
- the electrodes comprise a central needle and six peripheral needles, regularly distributed on a circle centered on the central needle;
- the voltage of the applied pulses is proportional to the distance, separating the two needles between which it is applied;
- each needle is separated from its neighbors by a distance of 4 to 10 mm, and preferably 6.5 mm.
- each electric pulse is a rectangular pulse of amplitude 100 to 1500 V and pulse length 10 to 200 µs;
- the needles of the electrodes are hollow and allow the active substance to be injected locally into the treatment volume;
- the needle holder carries a syringe associated with each needle, said syringe being formed of a body and a piston;
- the needle selector switch comprises two relays associated with each needle, said selector switch being able to connect the needle to the positive terminal or negative terminal of the pulse generator;
- the applicator comprises a control unit which can produce a given sequence of electric pulses as determined by the operator, following the injection of substance.

The invention will be better understood from the following detailed description of a particular embodiment of the invention.

BRIEF DESCRIPTION OF THE DRAWINGS

FIG. 3 is a partial cross-sectional view of a needle holder.

FIG. 6 is an above view of the bottom of the needle holder.

FIG. 7 is an above view of the insulating washer of the needle holder.

FIG. 8 is a cross-sectional view of the needle holder showing the electric link of the needle with the pulse generator.

DESCRIPTION OF THE PREFERRED EMBODIMENTS

Figure 1:
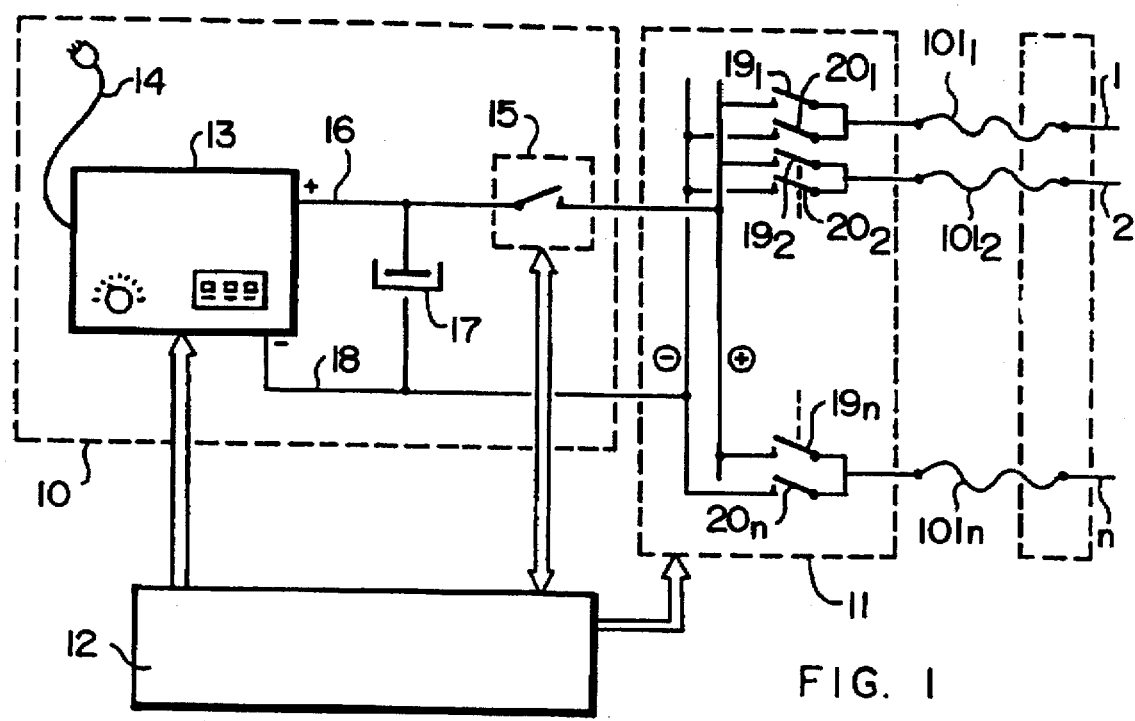
FIG. 1 is a schematic drawing of the general electric circuit of the invention.

Since the needles are all structurally identical and associated with the same elements, each of these elements is designated by a single reference irrespective of the needle to which it is intended. This reference may possibly be followed by an index corresponding to the reference number of the needle.

The electric pulse applicator for the electrochemotherapy biological tissue is intended to apply a variable electric field to cells located between a pair of needles 1, 2 . . . n.

To achieve this, it comprises a pulse generator 10, a selector switch 11 and a control unit 12. Pulse generator 10 comprises a high voltage power supply 13 which is connected to the mains supply by a mains cord 14, and to the selector switch via a switch 15 connected to the, generator's positive output, a capacitor 17 being connected in parallel across its positive output 16 and negative output 18.

Each electrode 1, 2, . . . n, can be connected either to the positive pole 16 of the high voltage power supply, or to its negative pole 18 by means of two relays $19_1$, $20_1$, $19_2$, $20_2$, . . . $19_n$, $20_n$ belonging to selector switch 11.

Control unit 12 controls the high tension power supply 13, switch 15 and changeover switch 11 according to the instructions it receives from an operator or via a program.

The electric pulse applicator is thus able to apply previously determined pulse cycles between needles 1, 2 . . . n in twos and in all possible combinations.

These cycles can be determined by any means, particularly experimental, in order to provide best possible results.

Preferably, relays $19_1$, $20_1$. . . $19_n$, $20_n$ are formed by a bar relay or REED bulb relay, the excitation for which is produced either by physical displacement of a small magnet whose position is slaved, or by a conventional command using a coil. This displacement is produced by a conventional position slaving system ensured by a coil.

Thanks to this arrangement, selector switch 11 can be made very compact.

For example, by closing relay $19_1$ and relay $20_n$, it is possible when switch 15 is closed to send a pulse between electrodes 1 and n, electrode 1 being the positive electrode and electrode n the negative electrode.

The electric contact is established with the tissue via the electrodes over all their non-insulated length, the produced field thus extending into the depth of the tissue. It is therefore possible to subject cells to electric fields which would not be accessible, at least not easily, from electrodes simply placed on the surface of the tissue.

Preferably, the pulses applied to each pair of needles are rectangular pulses having an amplitude of 100 to 1500 V and a pulse length of 10 to 200 μs. These pulses are spaced, for each pair of needles, by an adjustable interval in the range 0.2 to 2 seconds, and preferably 1 second.

For each pair of needles, it is possible, for example, to apply eight successive pulses of the same polarity, or four pulses of a first polarity followed later in the cycle by four pulses of the opposite polarity. In the case of electrodes comprising many needles, for example seven as in the embodiment described below, the pulse sequences concerning the different pairs of needles can be interleaved. Thus, given the length of each pulse and of the interval which must separate two successive pulses applied to a given pair of electrodes, it is possible to excite the different pairs of electrodes one after another while respecting these sequences.

The electric fields thus produced can be approximately uniformly distributed, including in depth, since the needles penetrate into the tissue and define therefore a set of elementary volumes of tissue, each of these volumes being included between two electrodes of a pair. By successively applying electric fields to these elementary volumes, good uniformity of treatment can be obtained over the whole volume of biological tissue treated.

Each needle 1, 2 . . . n, comprises a base 30, a head 31, a connector 32 comprising a flat surface and a base 33.

Base 33 carries stem 34 which is terminated by a point 35. One or more parts of stem 34 preferably comprise an insulating sleeve 36, made for example from PTFE (polytetrafluoroethylene) which provides, when inserted into tissue, a means of preventing the application of electric pulses to certain zones. In particular, it is often preferable to avoid applying the electric field to the surface.

In addition, according to a preferred embodiment, the part of this insulating sheath 36 in the visinity of the base is removable and can be left for a certain period of time in the tissue to facilitate use of the pulse applicator on several occasions when creating the same tissue volume, without any risk of damaging healthy superficial tissue and also, once the electric treatment has finished (at least provisionally), to continue with injecting one or more substances or medicamentous compositions (for example immunomodulators, such as interleukine-2 or secreting cells for example of interleukine-2). A further advantage of the catheter thus formed is that its flexibility allows it to be worn for a prolonged period without physical tissue lesion.

Advantageously, the needles are fixed onto a needle holder 40. This needle holder is, for example, generally circular in section, and comprises an upper plate 41, a bottom plate 42 and an insulating washer 43. Insulating plate 43 rests on bottom plate 42 which is connected to the upper plate by small columns 44 forming distance sleeves. These small columns 44 are screwed into bottom plate 42 and receive bolts 45 ensuring the fixing of upper plate 41. Inserts 46 are placed in the openings provided for this purpose in the bottom plate and insulating plate anti receive heads 31 of the needles. Heads 31 can, for example, be threaded, inserts 46 having a complementary thread. An external tool, not shown, is able to work with the flat surfaces of zone 32 of the needles, and can for example be used to facilitate the assembly and removal of needles in inserts 46.

An electrical connection 100 establishes link 46 between insert 46 and selector switch 11 via a wire 101. Advantageously, a seal 47 ensures a good link between needles 1, 2, . . . n, and inserts 46.

Each needle 1, 2 . . . n. is connected to selector switch 11 by means of the insert 46 on which is screwed, and is therefore able to be connected to pulse generator 10.

The upper plate comprises passages 44 for the small columns and passages 48 for the electric wires.

The insulating washer comprises passages 44 for the small columns and passages 49 to ensure its fixing onto the bottom plate.

According to the preferred embodiment, needles 1, 2 . . . n are hollow and can be used to locally inject a locally active substance.

For this purpose, needles 1, 2 . . . n are hollow and connected by means of inserts 46 to syringes 50 comprising a body 51 and a piston 52. Upper plate 41 bears against body 51 of the syringes and helps hold them in position.

This plate 41 comprises passages 53 allowing pistons 52 of syringes 50 to move freely.

An external cylinder 54 is advantageously provided and fixed to upper plate 41 on the one hand, and to bottom plate 42 on the other hand. This external cylinder surrounds the device thus protecting it and facilitating its handling. This external cylinder 54, on the one hand, bears against bottom plate 42 comprising a shoulder 60 provided for this purpose, and on the other hand is screwed on upper plate 41 by a screw 61 working with a thread 62 made in upper plate 41.

The hollow stem 34 of the needle comprises at least one opening at its end 35. In order to improve the homogeneous distribution of the injected substance throughout all the volume of the treated tissue, it also preferably comprises openings 37, 38 distributed at intermediate levels over its height. Such a needle is known as "fenestrated".

According to a further embodiment, the body of syringes 51 are conductors, for example, metallic, which makes it possible to simplify the electric links.

Pistons 52 are actuated by moveable rods 55. Rods 55 are, for example, screwed onto piston 52 and can be unscrewed.

The needles are therefore supplied with electric power via syringe bodies 51. Their upper portion forms a female electric contact which works with a male plug holder 56 connected to selector switch 11.

Rods 55 are first of all fixed onto pistons 52 to allow the injection to be performed. They are then removed and the plug holder connected onto syringe bodies 51. Electrical pulses can now be applied.

Figure 5:
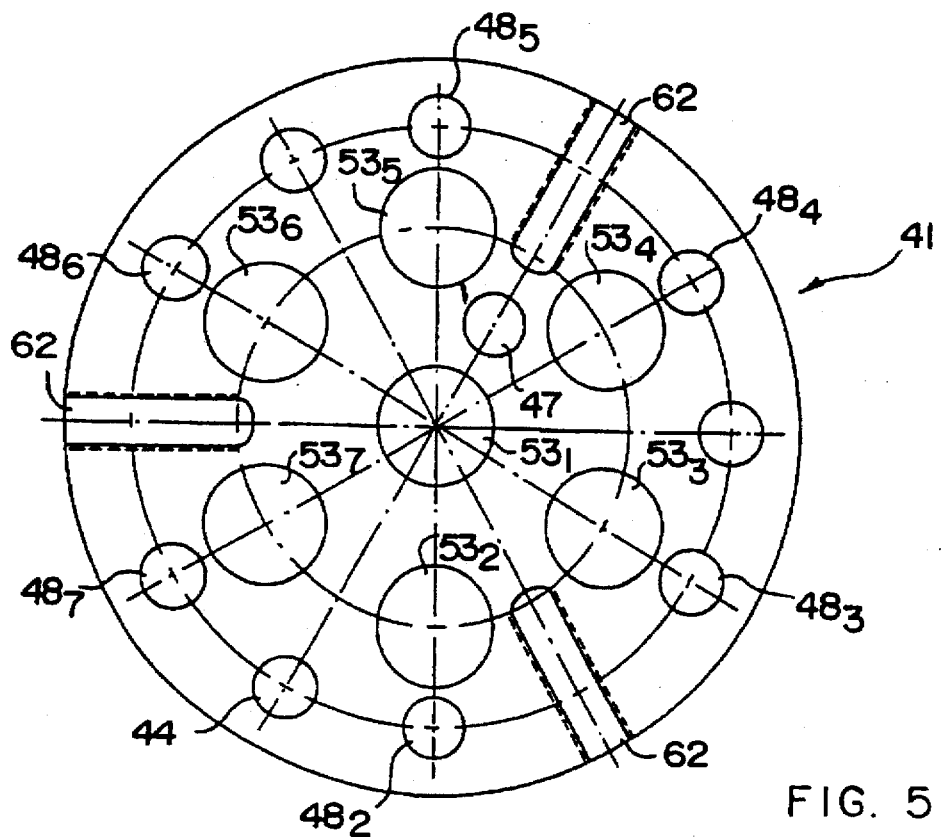
FIG. 5 is an above view of the upper plate of the needle holder.
Figure 4:
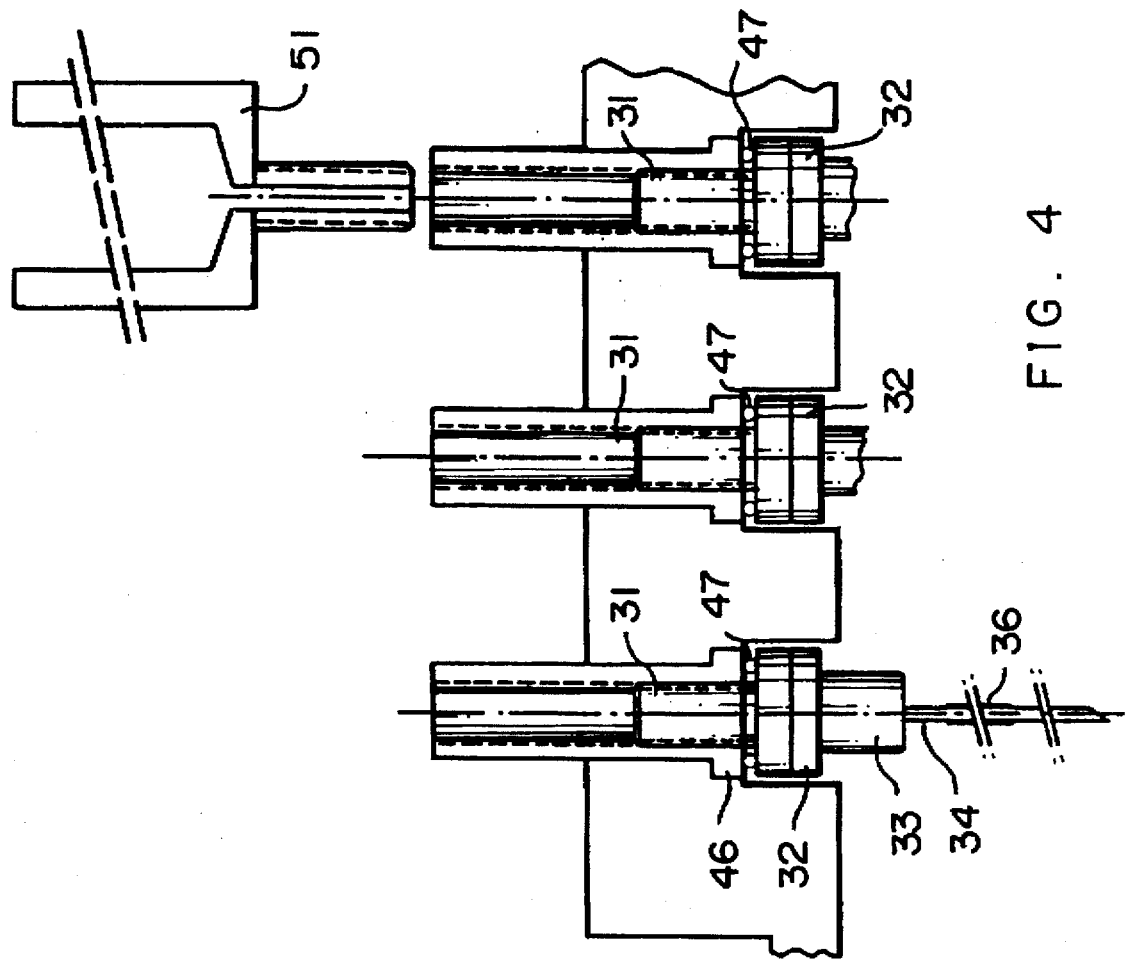
FIG. 4 is a cross-sectional view of the fixing of a needle onto the needle holder.
Figure 2:
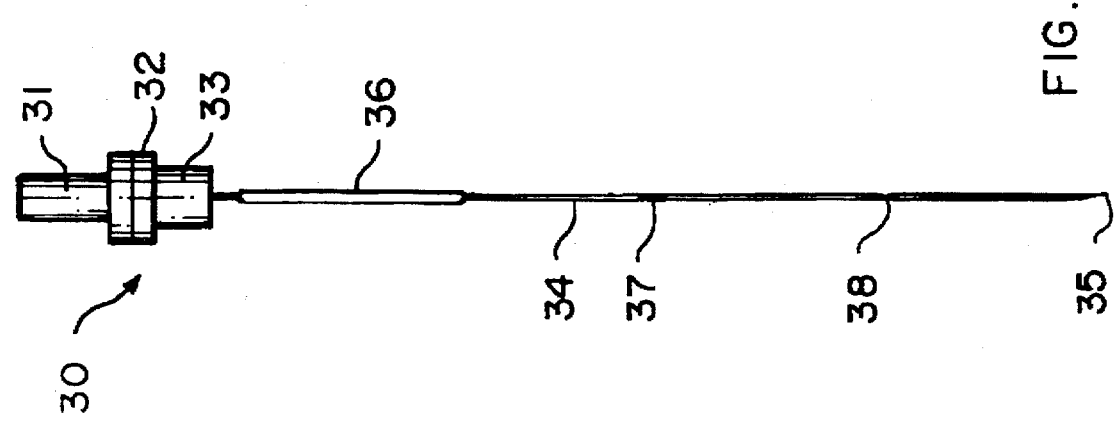
FIG. 2 is a cross-sectional view of a needle.
Figure 10:
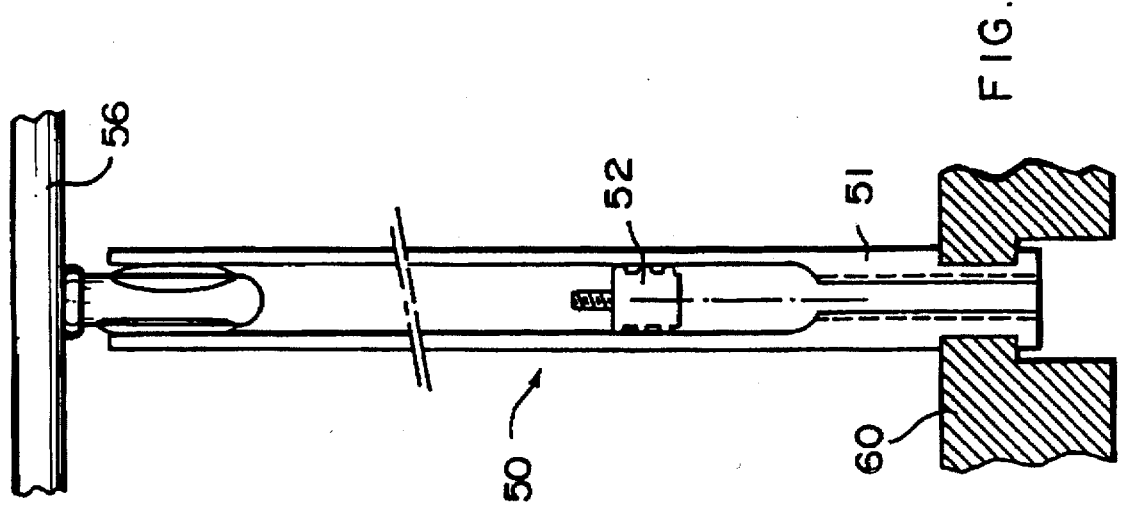
FIG. 10 is a partial cross-sectional view of a syringe with a conducting body in the electric field application state.
Figure 9:
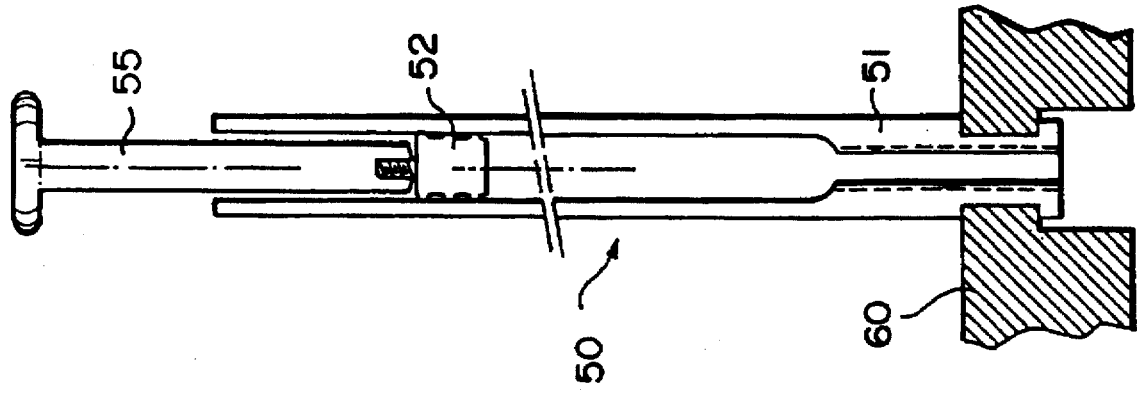
FIG. 9 is a partial cross-sectional view of a syringe with a conducting body in the injecting state.

FIGS. 5, 6 and 7 show the distribution of the needles and syringes when seven of them are simultaneous used. One of them 1 is arranged al: the center and the other six 2–7 equally distributed on a circle centered on the first.

Advantageously, derived distributions could be used when a larger number of needles are used. For example, nineteen needles could be used by placing the twelve additional needles on a second crown concentric with the first circle, the radius of the second crown being approximately double that of the first circle. Thirty-seven needles can be distributed by distributing, with respect to the first circle, the eighteen additional needles uniformly around a third crown concentric with the first circle, the radius of the third crown being approximately three times that of the first circle, in such a way that all pairs comprising a given needle and all those surrounding it are equidistant.

If the needles are not equidistant, the voltage of the applied pulse; will depend on the spacing of the pair of needles to which it is intended. This voltage is preferably proportional to the spacing.

The characteristics of the electric pulses can generally be determined with a view to a particular protocol. They are not necessary rectangular.

The electric pulse applicator can therefore be used in the following way. Syringes 50 are first of all filled with the solution containing the active substance to be injected.

The device is then placed in position by introducing the needles into the tissue to be treated.

The active substance is then injected.

After a waiting period determined by experience, control unit 12 is triggered and the electric pulse sequences activated so as to produce the desired intensities of electric field at the heart of the tissue located between or in the vicinity of the needles. At the end of the electric treatment, the needles are withdrawn, the insulating sleeves being, if necessary, left in place to allow substances or medicamentous compositions to be injected at a later time.

Other variations can be envisaged with respect to the above; embodiment without leaving the scope of the claims. In particular, the control of the generator can be performed from a distance and, for example, from a trigger mounted on the applicator.

Moreover, the shape of the electric pulses could be modified and adapted according to experimental results.

The reference numerals inserted after the characteristic features mentioned in the claims are merely intended to facilitate the understanding of the latter without limiting at all the range claimed.

We claim:

1. Electric pulse applicator for the treatment of biological tissue allowing an electric field to be applied to cells of biological tissue in such a way as to modify properties of their membrane, comprising:

electrodes, the electrodes including at least three needles intended to be introduced into the tissue to be treated and which define a treatment volume, said needles in twos forming pairs of needles;

a pulse generator sending pulses to the electrodes, the pulse generator having a negative pole and a positive pole;

a selector switch connected to and arranged between the pulse generator and the electrodes, the selector switch being able to connect each needle with either the negative pole or the positive pole of the pulse generator and thereby can direct the pulses produced by the pulse generator successively onto all the different pairs of needles; and a control mechanism connected to the selector switch and pulse generator for controlling the pulse generator and the selector switch so as to form any pairs of needles among the needles.

2. The electric pulse applicator of claim 1, wherein the electrodes comprise a central needle and six peripheral needles regularly distributed on a circle centered on the central needle.

3. The electric pulse applicator of claim 1, wherein said pulses comprise a voltage which is proportional to a distance separating the two needles between which the voltage is applied.

4. The electric pulse applicator of claim 1, further comprising a control unit connected to the selector switch.

5. The electric pulse applicator of claim 1, wherein each needle is separated from its neighbors by a distance of 4 to 10 mm.

6. The electric pulse applicator of claim 5, wherein each needle is separated from its neighbors by a distance of 6.5 mm.

7. The electric pulse applicator of claim 1, wherein each needle has and is connected to first and second relays, each first and second relay forming a portion of the selector switch.

8. The electric pulse applicator of claim 7, wherein said selector switch comprises means for activating each first relay to connect each needle to the positive terminal of the pulse generator, said selector switch also comprises means for activating each second relay to connect each needle to the negative terminal of the pulse generator.

9. The electric pulse applicator of claim 1, wherein the needles of the electrodes are fixed onto a needle holder in an interchangeable way.

10. The electric pulse applicator of claim 9, wherein the needles each comprise a base and a stem terminated by a point, the base ensuring the fixing of the needle onto the needle holder, the point ensuring the penetration of the needle into the tissue, at least one portion of the stem being surrounded by an insulating sleeve.

11. The electric pulse applicator of claim 10, wherein a removable portion of the insulating sleeve of the needles forms a catheter capable of being implanted in the tissue.

12. The electric pulse applicator of claim 1, wherein each pulse comprises a rectangular pulse having an amplitude of 100 to 1500 V and a pulse length of 10 to 200 microseconds.

13. The electric pulse applicator of claim 12, further comprising a control unit which can produce an electric pulse sequence to control the selector switch as determined by an operator.

14. The electric pulse applicator of claim 13, wherein the control unit comprises a program for generating the electric pulse sequence to control the selector switch following the injection of a substance.

15. The electric pulse applicator of claim 13, wherein the control unit is also connected to a power supply which is connected to the pulse generator, the control unit further being connected to another switch which is between the pulse generator and the selector switch.

16. The electric pulse applicator of claim 1, wherein the needles of the electrodes include hollow passages for allowing an active substance to be injected locally into the treatment volume.

17. The electrode pulse applicator of claim 16, wherein the needles of the electrodes comprise fenestrated needles.

18. The electric pulse applicator of claim 17, further comprising a needle holder connected to the needles.

19. The electric pulse applicator of claim 17, wherein a needle holder comprises a holder mechanism allowing the needle holder to carry a syringe associated with each needle, said syringe being formed of a body and a piston, the piston being connected with the body.

20. The electric pulse applicator of claim 19, wherein the holder mechanism includes at least one plate having openings which allow the needle holder to carry the syringe.

21. The electric pulse applicator of claim 19, wherein the body of the syringe comprises a hollow body and wherein the piston is fitted into the hollow body.

* * * * *